(12) United States Patent
Li et al.

(10) Patent No.: US 7,618,938 B2
(45) Date of Patent: Nov. 17, 2009

(54) TREATING CEREBROVASCULAR DISEASES WITH ERYTHROPOIETIN AND GRANULOCYTE-COLONY STIMULATING FACTOR JOINTLY

(75) Inventors: Hung Li, Taipei (TW); Woei-Cherng Shyu, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 11/703,578

(22) Filed: Feb. 7, 2007

(65) Prior Publication Data

US 2008/0188407 A1    Aug. 7, 2008

(51) Int. Cl.
A61K 38/18 (2006.01)
A61K 38/19 (2006.01)
C07K 14/535 (2006.01)
C07K 14/505 (2006.01)

(52) U.S. Cl. .......................... 514/2; 530/350; 530/397; 530/399

(58) Field of Classification Search ................. None
See application file for complete search history.

(56) References Cited

U.S. PATENT DOCUMENTS

| 7,220,407 | B2 | 5/2007 | Mehta et al. | |
| 2003/0153503 | A1* | 8/2003 | Klaus et al. | 514/12 |

OTHER PUBLICATIONS

Ehrenreich et al. A novel role for an established player: anemia drug erythropoietin for the treatment of cerebral hypoxia/ischemia. Transfusion and Apheresis Science vol. 31:39-44 (2004).*
Shyu et al. Functional recovery of stroke rats induced by granulocyte colony-stimulating factor-stimulated stem cells. Circulation vol. 110:1847-1854 (Sep. 20, 2004).*
Ren et al. Growth factor and treatment of stroke. Current Drug Targets-CNS & Neurological Disorders vol. 4:121-125 (2005).*
Cerebrovascular Disease (Neurosurgerytoday.org; pp. 1-11; Dec. 2005). www.neurosurgerytoday.org/what/patient_e/cerebrovascular.asp.*
Casadevall et al., "Health, Economic and Quality-of-Life Effects of Erythropoietin and Granulocyte Colony-Stimulating Factor for the Treatment of Myelodysplastic Syndromes: A Randomized, Controlled Trial," *Blood*, 104:321-327 (2004).
Pierelli et al., "Erythropoietin Addition to Granulocyte Colony-Stimulating Facto Abrogates Life-Threatening Neutropenia and Increases Peripheral-Blood Progenitor-Cell Mobilization After Epirubicin, Paclitaxel, and Cisplatin Combination Chemotherapy: Results of a Randomized Comparison," *J. Clin. Oncol.*, 17:1288-1295 (1999).
Pierelli et al., "In Vitro and In Vivo Effects of Recombinant Human Erythropoietin Plus Recombinant Human G-CSF on Human Haemopoietic Progenitor Cells," *Bone Marrow Transplantation*, 14:23-30 (1994).
Pierelli et al., "The Combination of Erythropoietin and Granulocyte Colony-Stimulating Factor Increases the Rate of Haemopoietic Recovery with Clinical Benefit after Peripheral Blood Progenitor Cell Transplantation," *British Journal of Haematology* 92:287-294 (1996).
Signore et al., "Erythropoietin Protects Against 6-hydroxydopamine-induced Dopaminergic Cell Death," *Journal of Neurochemistry*, 96:428-443 (2006).
Villa et al., "Reduced Functional Deficits, Neuroinflammation, and Secondary Tissue Damage After Treatment of Stroke by Nonerythropoietic Erythropoietin Derivatives," *Journal of Cerebral Blood Flow & Metabolism*, advance online publication, Jul. 12, 2006; doi:10.1038/sj.jcbfm.9600370.
Wei et al., "Cell Death Mechanism and Protective Effect of Erythropoietin after Focal Ischemia in the Whisker-Barrel Cortex of Neonatal Rats," *The Journal of Pharmacology and Experimental Therapeutics*, 317(1):109-116 (2006).
Zhang et al., "Erythropoietin Protects CA1 Neurons Against Global Cerebral Ischemia in Rat: Potential Signaling Mechanisms," *Journal of Neuroscience Research* 83:1241-1251 (2006).

* cited by examiner

*Primary Examiner*—Marianne P Allen
*Assistant Examiner*—Regina M DeBerry
(74) *Attorney, Agent, or Firm*—Occhiuti Rohlicek & Tsao LLP

(57) ABSTRACT

A method for treating a cerebrovascular disease with erythropoietin (EPO) and granulocyte-colony stimulating factor (G-CSF) jointly by first identifying a subject in need of the treatment and then administering to the subject an effective combined amount of EPO and G-CSF. Also disclosed is a method for increasing in a subject expression of EPO with G-CSF.

19 Claims, No Drawings

TREATING CEREBROVASCULAR DISEASES WITH ERYTHROPOIETIN AND GRANULOCYTE-COLONY STIMULATING FACTOR JOINTLY

BACKGROUND

EPO, a 30.4-kDa glycoprotein, regulates production of erythrocytes. It stimulates the proliferation and differentiation of erythroid precursor cells through binding to EPO receptors expressed on the surface of these cells. See Krantz, Blood 77(3):419-434 (1991) and Jelkmann, Physiol Rev. 72(2):449-489 (1992). EPO is a well-known therapeutic agent for treating anemia resulting from chronic renal failure or cancer chemotherapy.

G-CSF, a 19.6-kD glycoprotein, stimulates bone marrow to produce granulocytes. In addition, it promotes survival, proliferation, differentiation, and function of neutrophil granulocyte progenitor cells and mature neutrophils. G-CSF has been used for treating neutropenia for over twenty years. See Burgess et al., Int. J. Cancer 26(5):647-654 (1980), and Frampton, et al., Drugs 48(5):731-760 (1994).

SUMMARY

The present invention is based on the unexpected discoveries that G-CSF up-regulates endogenous EPO expression via activating HIF-1α, a transcriptional factor of EPO, and that G-CSF and EPO act in synergism in treating a cerebrovascular disease.

Thus, within the scope of this invention is a method for treating a cerebrovascular disease (e.g., cerebral ischemia, stroke, cerebral infarct) with EPO and G-CSF jointly. This method includes first identifying a subject in need thereof and then administering to that subject an effective combined amount of EPO and G-CSF. EPO and G-CSF can be administered, e.g., by subcutaneous injection, either separately or simultaneously.

Also within the scope of this invention is a method of increasing the EPO level in a subject with G-CSF. This method includes identifying a subject in need thereof (e.g., an anemia patient) and administering to the subject an effective amount of G-CSF via the subcutaneous route or other routes.

The details of one or more embodiments of the invention are set forth in the description below. Other features, objects, and advantages of the invention will be apparent from the description and drawings, and from the claims.

DETAILED DESCRIPTION

The expression of EPO can be up-regulated by transcriptional factor hypoxia-inducible factor-1α (HIF-1α) through its binding to the hypoxia-response element, a conserved sequence (5'-RCGTG-3') presented in the promoter of EPO. See Semenza, Trends Mol Med. 7(8):345-350, 2001.

The inventors have discovered that G-CSF enhances the expression of EPO via activating HIF-1α. They have also found that EPO and G-CSF, when used jointly, show synergistic neuroprotective effect in primary cortical cells. For example, EPO and G-CSF in combination inhibited apoptosis by increasing the expression of Bcl-2 (an anti-apoptotic protein) and blocking the activity of caspase-3 (a major player in apoptosis). This joint effect is significantly greater than the individual effect of either EPO or G-CSF in inhibiting neuron cell apoptosis. Further, co-administration of EPO and C-GSF show synergistic effect in reducing ischemic injury. EPO and G-CSF in combination significantly reduce cerebral infarction and improve neurological dysfunction following middle cerebral artery ligation. EPO and G-CSF in combination also significantly enhance the number of stem cells mobilized to the ischemic sites after ischemia. Moreover, EPO and G-CSF in combination promoted angiogenesis and new cerebral blood vessel formation in ischemic brains. In sum, the above-described discoveries clearly indicate that EPO and G-CSF act in synergism in treating cerebralvascular diseases.

Treating a cerebrovascular disease is accomplished by first identifying a subject in need of this treatment and then co-administering to that subject an effective combined amount of EPO and G-CSF.

Cerebrovascular disease includes all disorders in which an area of the brain is transiently or permanently affected by ischemia or bleeding and one or more of the cerebral blood vessels are involved in the pathological process.

"An effective combined amount" refers to the combined amount of EPO and G-CSF that is required to confer a therapeutic effect on the treated subject. Effective doses will vary, as recognized by those skilled in the art, depending on the types of diseases treated, route of administration, carrier usage, and the possibility of co-usage with other therapeutic treatment.

EPO and G-CSF can be obtained from commercial sources, e.g., Johnson & Johnson, and Kirin Pharmaceuticals Co. Ltd. They can also be isolated from natural sources or produced by recombinant DNA technologies.

EPO and G-CSF can be formulated either separately as two pharmaceutical compositions or together as one pharmaceutical composition. The composition(s) includes a pharmaceutically acceptable carrier. "Acceptable" means that the carrier is compatible with the active ingredient of the composition (and preferably, capable of stabilizing the active ingredient) and not deleterious to the subject to be treated. One or more solubilizing agents can be utilized as the pharmaceutical carrier. Examples of other carriers include colloidal silicon oxide, magnesium stearate, cellulose, sodium lauryl sulfate, and D&C Yellow # 10.

To practice the above-described treatment, EPO and G-CSF can be administered via various routes, such as the parenteral route. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique. EPO and G-CSF can be administered simultaneously whether they are formulated separately or together or sequentially when they are formulated separately.

In one example, EPO and G-CSF are formulated together as a sterile injectable composition. This composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

The present invention also features the use of EPO and G-CSF jointly in a medicament for treating a cerebrovascular disease.

Another aspect of this invention relates to increasing expression of EPO in a subject by first selecting a subject in need thereof and then administering to that subject an effective amount of G-CSF. A subject will need increased expression of EPO in various scenarios, e.g., suffering anemia. G-CSF can be formulated and administered by the same manner as described above. Also within the scope of this invention is the use of G-CSF in a medicament for increasing EPO expression in a subject.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

G-CSF Increased the Serum EPO Levels in Healthy Donors

Healthy donors were administered with G-CSF (10 µg/kg) by subcutaneous injection for five consecutive days. Blood samples were collected from these donors at day 1, day 3, day 7, and day 14 after G-CSF administration. The levels of EPO in these blood samples were measured by ELISA assays, using an EPO-specific antibody purchased from R&D Systems, Minneapolis, Minn.

G-CSF significantly increased the serum EPO levels, which peaked at day 3 after G-CSF injection.

EXAMPLE 2

G-CSF Activated HIF-1α to Upregulate the Expression of EPO in Primary Cortical Cultures Rat primary cortical cells were isolated from the cerebral cortex of gestation day 17 embryos of Sprague-Dawley rats following the method described in Goldberg et al., J. Neurosci. 13(8):3510-3524. Four days after isolation, the primary cortical cells were replenished with minimum essential medium (GIOCO-BRL) containing 0.5 g/L BSA, 2% B27 supplement, 0.5 mM pyruvate and antibiotics (i.e., penicillin G at $10^5$ U/L and streptomycin at 100 mg/L). On day 7, the culture medium was replaced with serum-free neurobasal medium containing 1 mM pyruvate, 1 mM glutamate, 0.5 g/L BSA, 2% B27 supplement and antibiotics (i.e., penicillin G at $10^5$ u/L and streptomycin at 100 mg/L).

The primary cortical cells were then treated with G-CSF for different periods of times (0.5 hour, 1 hour, 4 hours, 10 hours, and 24 hours) and at different dosages (0.01 µg/ml, 0.1 µg/ml, 1 µg/ml, and 10 µg/ml). After treatment, the cells were lysed in a buffer containing 320 mM sucrose, 5 mM HEPES, 1 µg/ml leupeptin, 1 µg/ml aprotinin and were centrifuged at 13,000 g for 15 minutes. The resultant pellet was suspended in a sample buffer containing 62.5 mM Tris-HCl, 10% glycerol, 2% SDS, 0.1% bromophenol blue, and 50 mM DTT and subjected to SDS-polyacrylamide gel (4-12%) electrophoresis. Proteins on the gel were then transferred to a Hybond-P nylon membrane and the levels of HIF-1α and EPO were determined by Western blot, using anti-HIF-1α and anti-EPO antibodies purchased from R&D Systems, Inc. The intensity of each protein band shown in the Western blot assay was measured by Kodak Digital Science 1 D Image Analysis System (Eastman Kodak, Rochester, N.Y.).

The levels of HIF-1α and EPO were clearly increased when the primary cortical cells have been treated with G-CSF for 1 hour and for 4 hours. This activation was also dose-dependent. The level of HIF-1α reached its peak at the dosage of 0.1 µg/ml G-CSF. The EPO level was increased when 0.1 µg/ml G-CSF was used and peaked at the dosage of 1 µg/ml G-CSF.

EXAMPLE 3

Synergistic Anti-Apoptotic Effects of EPO and G-CSF in Primary Cortical Cells

Rat primary cortical cells were isolated and cultured according to the methods described above. To test the anti-apoptotic effects of EPO and G-CSF, these cells were first treated with G-CSF (2 µg/ml), EPO (20 U/ml), or [G-CSF (1 µg/ml)+EPO (10 U/ml)] for 12 hours, and then subjected to oxygen glucose deprivation (OGD) treatment to induce apoptosis. Briefly, cells cultured in glucose-free Earle's balanced salt solution were placed in a hypoxic chamber (Bug Box, Ruskinn Technology, UK) for four hours. During this period, the cells were continuously flushed with 95% $N_2$ and 5% $CO_2$ at 37° C. so that the pressure of oxygen is less than 1 mmHg. Then the ODG-treated cells were re-oxygenated for 24 hours and cultured under normal culturing conditions as discussed above. Control cells were incubated in glucose-free Earle's balanced salt solution in a normoxic incubator for the same time period.

After ODG treatment, the cortical cells were examined for caspase-3 activity by fluorometric assays, using a commercially available kit (Bio-Rad). The expression of apoptosis-related proteins, e.g., Bcl-2, Bcl-xL, Bax, and Bad, in these cells were also determined by Western blot.

Primary cortical cells treated with either EPO at 20 U/ml or G-CSF at 2 µg/ml showed significantly reduced caspase-3 activity under OGD-induced neurotoxic conditions. The caspase-3 activity was further reduced in cells treated with [EPO (10 U/ml)+G-CSF (1 µg/ml)]. Clearly, the treatment of EPO and G-CSF jointly showed synergistic effects in reducing caspase-3 activity in OGD-treated cortical cells, compared to the treatment of either EPO or G-CSF separately.

Similarly, both EPO (20 U/ml) and G-CSF (2 µg/ml) activated the expression of Bcl-2 in ODG-treated cortical cells. The level of Bcl-2 was further increased when cells were treated with [EPO (10 U/ml)+G-CSF (1 µg/ml)] jointly.

EXAMPLE 4

EPO and G-CSF Synergistically Improved Neurological Behavior after Cerebral Ischemia Body swing tests and locomotor activity tests were performed to determine the effects of EPO, G-CSF, and [EPO+ C-GSF] in rescuing rats from ischemic insult.

In vivo brain ischemia/reperfusion was performed on 40 adult male Sprague-Dawley rats (weight 250-300 g, age 6-7 weeks). The rats were anesthetized with chloral hydrate (0.4 g/kg, ip) and subjected to right middle cerebral artery (MCA) ligation and bilateral common carotid artery (CCA) clamping as described in Chen et al., A model of focal ischemic stroke in the rat: reproducible extensive cortical infarction. *Stroke*, 17(4):738-743 (1986). After 90 minutes of ischemia induction, the 10-0 suture on the MCA and arterial clips on CCAs were removed to allow reperfusion. When rats were recovering from anesthesia, their body temperature was maintained at 37° C. with a heat lamp. One day after the induction of cerebral ischemia, the rats were subdivided into four groups (10 in each group), each of which was treated with G-CSF (100 µg/kg), EPO (10,000 U/kg), [G-CSF (50 mg/kg)+EPO (5,000 U/kg)], or vehicle control respectively by subcutaneous injection.

Behavioral assessments of the rats were performed 3 days before, and 3, 7, 14, and 28 days after the induction of ischemia. These assessments include: (a) performing body swing test according to the method described in Borlongan et al., Neuroreport 9(12):2837-2842, (b) determining locomotor activity as described in Shyu et al., Circulation 110(13):1847-1854 (2004), and (c) measuring grip strength using a Grip Strength Meter as described in Dunnett et al., Neurosci Lett. 246(1):1-4 (1998), with modifications. In brief, the grip strength of each forelimb was measured separately before and after treatment. Then the mean strengths (out of 20 pulls) were calculated. The grip strength ratio refers to the comparison between the mean strength of the side contralateral to the ischemic site and that of the ipsilateral side.

Several days after the induction of cerebral ischemia, rats treated with vehicle control exhibited severe body asymmetry. This abnormality was significantly reduced in rats treated with EPO (10,000 U/kg), G-CSF (100 µg/kg) or EPO (5,000 U/kg) and G-CSF (50 µg/ml). The recovery rate of rats treated with EPO and G-CSF jointly was much higher than that of rats treated with either EPO or G-CSF separately. This result showed the synergistic effect of EPO and G-CSF in rescuing rats from ischemia insult.

Rats suffered ischemia displayed impaired locomotor activities, which were measured by vertical activity, number of vertical movement, and time that each vertical movement has lasted. These activities were significantly recovered in ischemic rats treated with EPO, G-CSF, or EPO and G-CSF. For example, at day 28 after treatment, the number of vertical movement in control rats was about 150. In rats treated with either EPO or G-CSF, this number increased to about 225. It increased to about 280 in rats treated with EPO and G-CSF jointly.

Ischemic rats treated with EPO and G-CSF jointly also showed a higher ratio of grip strength than that of rats treated with either EPO or G-CSF individually or with vehicle control.

EXAMPLE 5

EPO and G-CSF Reduced Infarct Volume after Cerebral Infarct

Cerebral ischemia was induced in rats following the method described above. Four groups of the ischemic rats (10 in each group) were treated with G-CSF (100 µg/kg), EPO (10,000 U/kg), [G-CSF (50 mg/kg)+EPO (5,000 U/kg)], or vehicle control respectively by subcutaneous injection. At day 7 after the induction, infarct areas in the right cortex of these ischemic rats were measured by MRI, using an imaging system produced by General Electric at 3.0 T. Briefly, rats were anesthetized with chloral hydrate and then each rat brain was subjected to six consecutive 3 mm thick coronal images. T2-weighted imaging (T2WI) pulse sequences were obtained with the use of a spinecho technique (repetition time: 4000 ms; echo time: 105 ms) and were captured sequentially for each animal at day 1, day 7, day 14, and day 28 after the induction of cerebral ischemia. The noninfarcted area in the right cortex were subtracted from the total cortical area of the left hemisphere of rat brains. The area of infarct was drawn manually from slice to slice, and the volume was then calculated by an internal volume analysis software (Voxtool, General Electric, Medical Systems, Fairfield, Conn.).

The infarct volumes in rats treated with EPO and G-CSF jointly were significantly smaller than that in rats treated with either EPO and G-CSF individually or with saline control. At day 7 after the induction of ischemia, the infarct volume in control rats (treated with saline) was 159±32 mm$^3$. Surprisingly, the infarct volume in rats treated with [EPO (5,000 U/kg)+G-CSF (50 µg/kg)] was 42±23 mm$^3$, which was much lower than those in rats treated with 10,000 U/kg EPO (77±26 mm$^3$) or with 100 µg/kg G-CSF (71±26 mm$^3$) separately. The number of infarct slices in rats treated with EPO and G-CSF jointly was also significantly lower than those in rats treated with EPO or G-CSF separately.

EXAMPLE 6

Effects of EPO and G-CSF on Stem Cell Mobilization and Differentiation in Ischemic Brain BrdU labeling was applied seven days after the induction of ischemia as described above to study the mobilization of both intrinsic neural progenitor cells (INPC) and bone marrow derived stem cells (BMSC). BrdU, a thymidine analog, incorporates into DNAs in dividing cells during DNA synthesis. It is routinely used to label mitotic cells. The labeling protocol and quantification of BrdU positive cells has been described in Zhang, et al., Neuroscience 105(1):33-41 (2001).

Ischemic rats were treated with EPO (10,000 U/kg), G-CSF (100 µg/kg), [EPO (5,000 U/kg)+G-CSF (50 µg/kg)], or saline. These rats were then subjected to BrdU labeling. In rats treated with EPO and G-CSF, either separately or jointly, immunohistochemical analysis revealed a few Brdu positive cells in the ipsilateral cortex nearby the infarct boundary and the subventricular region of the ischemic hemisphere. BrdU positive cells were also found around the lumen of varying calibers of blood vessels in the perivascular portion of the ischemic hemisphere. The number of BrdU positive cells found in rats treated with EPO and G-CSF jointly was significantly higher than those in rats treated with either EPO or G-CSF separately.

Bone marrow transplantation assays were performed to study stem cell differentiation in ischemic mice treated with EPO, G-CSF or EPO and G-CSF. Bone marrow was extracted from GFP-transgenic donor mice following the procedures described in Hess et al., Stroke 33(5):1362-1368 (2002). Briefly, bilateral ends of the femurs and tibias were penetrated using a syringe with a 25-gauge needle, allowing the marrow to be flushed out with sterile saline. Marrow from 1 femur was diluted to 1 ml then strained through 30 µm Spectramesh (Fisher Scientific, Suwanee, Ga.).

Before bone marrow transplantation, the male recipient mice underwent gamma irradiation with $^{137}$CS using a Gammacell 40 irradiator (MDS Nordion, Ottawa, Ontario, Canada). A total dose of 9 Gy was administered to ablate the whole bone marrow in the recipient mice. Since high levels of radiation might significantly increase death rates during and immediately after induction of cerebral ischemia, the recipient mice received rescuing bone marrow transplantation within 24 hours after irradiation.

Bone marrow (100 µl containing 1-1.5×10$^6$ cells) was then injected into tails of the recipient mice. Three to six weeks after transplantation, the recipient mice were anesthetized with chloral hydrate (0.3 g/kg. ip) and subjected to induction of cerebral ischemia as described above. One day after the induction of ischemia, these mice were divided into four groups, each group being subcutaneously injected with EPO (10,000 U/kg), G-CSF (10 μg/kg), [EPO (5,000 U/ml)+G-CSF (5 μg/kg)], or vehicle control, once a day for five consecutive days. BrdU labeling was also performed on each mouse following the above-described procedures.

Next, brain slices of mice from each group were stained with antibodies specific to BrdU, as well as to glial fibrillary acidic protein (GFAP), von Willebrand factor (vWF), microtubule-associated protein 2 (MAP-2), neuronal nuclei (Neu-N), and Musashi-1. $GFP^+$ and $BrdU^+$ cells were detected under a laser-scanning confocal microscope.

$GFP^+$ cells were found to be dispersed over the bilateral striatum, hippocampus and the penumbral area in mice treated with EPO, G-CSF, and EPO and G-CSF, but not in mice treated with vehicle control. Brain slices derived from mice treated with EPO and G-CSF jointly showed a significantly increased number of $GFP^+$ and $BrdU^+$ cells compared to those in mice treated with either EPO or G-CSF individually. In addition, hippocampus, subventricular and ischemic penumbral areas of rats treated with EPO and G-CSF revealed an increase of $BrdU^+$ cells that were co-expressed with GFAP, Neu-$N^+$, and MAP-2. $GFP^+$-Musashi-$1^+$-$BrdU^+$ cells were almost only found in the hippocampus.

EXAMPLE 7

Subcutaneous EPO and G-CSF Injection Induced Angiogenesis in Ischemic Brain

Cerebral microcirculation was analyzed using FITC-dextran, a fluorescent plasma marker. This marker was intravenously injected into ischemic rats treated with EPO (10,000 U/kg), G-CSF (100 μg/kg), [EPO (5,000 U/kg)+G-CSF (50 μg/kg)], or vehicle control, and detected using a fluorescent microscope as described in Morris et al., Brain Res. Brain Res. Protoc 4(2):185-191 (1999).

The results of FITC-dextran perfusion indicated that treatment with EPO and G-CSF (n=6) had induced much more cerebral microvascular perfusion than treatment with EPO (n=6), G-CSF (n=6), or vehicle control (n=6).

The following procedures were performed to quantify the density of cerebral blood vessels. The ischemic rats were anesthetized with chloral hydrate and perfused with saline. Histological sections (6 μm) were stained with an Cy-3-conjugated antibody specific to CD31 (PharMingen, San Diego, Calif.). The number of cerebral blood vessels was then determined as described in Taguchi, et al., J. Clin. Invest. 114(3): 330-338 (2004).

CD31 immunostaining showed that ischemic rats treated with EPO, G-CSF, and EPO and G-CSF displayed a significant increase of neovasculature in their penumbral area. The number of blood vessels in rats treated with EPO and G-CSF jointly was much higher than those in rats treated with either EPO or G-CSF individually.

EXAMPLE 8

EPO and G-CSF Facilitated Cerebral Blood Flow (CBF) in Ischemic Brain

Rats anesthetized with chloral hydrate were positioned in a stereotaxic frame and baseline local cortical blood flow (bCBF) was monitored after cerebral ischemia using a laser Doppler flowmeter described in Part et al., J. Neurosci. 25(7): 1769-1777 (2005). CBF values were calculated as a percentage increase of bCBF after the treatment of with EPO (10,000 U/kg), G-CSF (100 μg/kg), [EPO (5,000 U/kg)+G-CSF (50 μg/kg)], or vehicle control.

Ischemic rats treated with EPO, G-CSF, EPO and G-CSF or vehicle control were monitored using laser Doppler flowmetry (LDF) under anesthesia. One week after cerebral ischemia, CBF values were significantly increased in the middle cerebral artery cortex of rats treated with EPO and G-CSF (n=6) compared with rats treated with EPO (n=6), G-CSF (n=6) or vehicle control (n=6).

EXAMPLE 9

Subcutaneous EPO and G-CSF Treatment did not Affect Physiological Parameters

Systemic physiological parameters, e.g., blood pressure, heart rate, blood glucose, and blood gas, were measured in 31 rats treated with EPO and G-CSF following a procedure described in Lin et al., Stroke, 30(1):126-133 (1999). All measurements in this example were performed blindly. Results are expressed as mean±SEM. The behavioral scores were evaluated for normality.

Table 1 shows the physiological parameters derived from EPO and G-CSF treated rats. There was no difference in systemic blood pressure, blood gases, blood glucose, or serum electrolyte levels between rates treated with vehicle control and rats treated with EPO (n=8), G-CSF (n=8), or EPO and G-CSF (n=8).

TABLE 1

Physiological parameters were not altered by any treatment

| Items | G-CSF + EPO (n = 7) | G-CSF (n = 8) | EPO (n = 8) | Vehicle (n = 8) | p* |
|---|---|---|---|---|---|
| pH | 7.34 ± 0.033 | 7.36 ± 0.04 | 7.31 ± 0.031 | 7.35 ± 0.039 | 0.711 |
| $PaCO_2$, mm Hg | 47.42 ± 2.37 | 51.36 ± 2.9 | 48.11 ± 1.77 | 49.12 ± 3.35 | 0.753 |
| $PaO_2$, mm Hg | 91.31 ± 4.3 | 92.57 ± 3.7 | 92.66 ± 3.9 | 93.07 ± 3.3 | 0.885 |
| $HCO_3^-$ ($10^{-3}$ mol/L) | 26.7 ± 2.57 | 25.66 ± 2.54 | 25.52 ± 2.11 | 26.0 ± 1.97 | 0.689 |
| Hematocrit, % | 44.33 ± 3.5 | 43.8 ± 2.75 | 44.08 ± 3.15 | 43.66 ± 3.0 | 0.611 |
| Hemoglobin (10 g/L) | 14.9 ± 0.62 | 15.39 ± 0.12 | 15.11 ± 0.32 | 14.79 ± 0.24 | 0.455 |
| $Na^+$ ($10^{-3}$ mol/L) | 138.5 ± 3.3 | 140.41 ± 2.9 | 139.31 ± 3.9 | 141.2 ± 3.0 | 0.543 |
| $K^+$ ($10^{-3}$ mol/L) | 4.23 ± 0.11 | 4.44 ± 0.45 | 4.3 ± 0.31 | 4.29 ± 0.21 | 0.759 |
| $Ca^+$ ($10^{-2}$ g/L) | 4.11 ± 0.41 | 3.94 ± 1.13 | 4.02 ± 0.22 | 3.98 ± 0.11 | 0.684 |
| Glucose ($10^{-2}$ g/L) | 151.2 ± 26.4 | 147.61 ± 15.2 | 150.4 ± 27.1 | 149.2 ± 21.4 | 0.621 |

TABLE 1-continued

Physiological parameters were not altered by any treatment

| Items | G-CSF + EPO (n = 7) | G-CSF (n = 8) | EPO (n = 8) | Vehicle (n = 8) | p* |
|---|---|---|---|---|---|
| MBP, mm Hg | 78.4 ± 7.51 | 83.2 ± 6.89 | 79.5 ± 8.12 | 80.4 ± 8.8 | 0.672 |
| HR, bpm | 398 ± 28 | 409 ± 17 | 401 ± 28.9 | 399 ± 26.8 | 0.821 |

MBP = mean blood pressure;
HR = heart rate;
*= t test

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method for treating a cerebrovascular disease, the method comprising administering to a subject in need thereof an effective combined amount of erythropoietin (EPO) and granulocyte-colony stimulating factor (G-CSF), wherein the cerebrovascular disease is cerebral ischemia or stroke and the EPO and G-CSF are administered simultaneously through a parenteral route.

2. The method of claim 1, wherein the cerebrovascular disease is cerebral ischemia.

3. The method of claim 2, wherein the EPO and G-CSF are formulated separately.

4. The method of claim 3, wherein the EPO and G-CSF are administered subcutaneously.

5. The method of claim 3, wherein the EPO and G-CSF are administered intravenously or intramuscularly.

6. The method of claim 2, wherein the EPO and G-CSF are administered subcutaneously.

7. The method of claim 2, wherein the EPO and G-CSF are administered intravenously or intramuscularly.

8. The method of claim 2, wherein the EPO and G-CSF are formulated in one pharmaceutical composition.

9. The method of claim 8, wherein the EPO and G-CSF are administered subcutaneously.

10. The method of claim 8, wherein the EPO and G-CSF are administered intravenously or intramuscularly.

11. The method of claim 1, wherein the cerebrovascular disease is stroke.

12. The method of claim 11, wherein the EPO and G-CSF are formulated separately.

13. The method of claim 12, wherein the EPO and G-CSF are administered subcutaneously.

14. The method of claim 12, wherein the EPO and G-CSF are administered intravenously or intramuscularly.

15. The method of claim 11, wherein the EPO and G-CSF are administered subcutaneously.

16. The method of claim 11, wherein the EPO and G-CSF are administered intravenously or intramuscularly.

17. The method of claim 11, wherein the EPO and G-CSF are formulated in one pharmaceutical composition.

18. The method of claim 17, wherein the EPO and G-CSF are administered subcutaneously.

19. The method of claim 17, wherein the EPO and G-CSF are administered intravenously or intramuscularly.

* * * * *